(12) United States Patent
Kobayashi

(10) Patent No.: US 8,604,434 B2
(45) Date of Patent: Dec. 10, 2013

(54) RADIATION IMAGING APPARATUS

(75) Inventor: Masaaki Kobayashi, Shimotsuke (JP)

(73) Assignee: Canon Kabushiki Kaisha, Tokyo (JP)

( * ) Notice: Subject to any disclaimer, the term of this patent is extended or adjusted under 35 U.S.C. 154(b) by 24 days.

(21) Appl. No.: 13/367,580

(22) Filed: Feb. 7, 2012

(65) Prior Publication Data

US 2012/0217395 A1    Aug. 30, 2012

(30) Foreign Application Priority Data

Feb. 28, 2011  (JP) ................................. 2011-042655

(51) Int. Cl.
*G01J 1/00* (2006.01)

(52) U.S. Cl.
USPC ..................................................... 250/336.1

(58) Field of Classification Search
USPC ................. 250/336.1–336.2, 370.01–370.15; 378/98.8
See application file for complete search history.

(56) References Cited

U.S. PATENT DOCUMENTS

| | | | | | |
|---|---|---|---|---|---|
| 4,380,087 | A | * | 4/1983 | Tanaka | 378/186 |
| 4,558,223 | A | * | 12/1985 | Broadhurst et al. | 250/374 |
| 5,008,920 | A | * | 4/1991 | Gralak | 378/185 |
| 5,440,130 | A | * | 8/1995 | Cox et al. | 250/370.09 |
| 5,804,832 | A | * | 9/1998 | Crowell et al. | 250/580 |
| 5,844,965 | A | * | 12/1998 | Galkin | 378/207 |
| 5,912,944 | A | * | 6/1999 | Budinski et al. | 378/182 |
| 6,013,723 | A | * | 1/2000 | Akao | 524/577 |
| 6,891,923 | B2 | * | 5/2005 | Tsujii | 378/62 |
| 6,895,080 | B2 | * | 5/2005 | Baba et al. | 378/154 |
| 7,254,214 | B2 | * | 8/2007 | Shoji | 378/98.8 |
| 7,302,039 | B2 | * | 11/2007 | Takenaka et al. | 378/98.12 |
| 7,359,482 | B2 | * | 4/2008 | Schmitt | 378/98.8 |
| 7,429,737 | B2 | * | 9/2008 | Wojcik et al. | 250/370.09 |
| 8,319,506 | B2 | * | 11/2012 | Liu et al. | 324/691 |
| 2002/0090055 | A1 | * | 7/2002 | Zur et al. | 378/154 |
| 2005/0151085 | A1 | * | 7/2005 | Caseault et al. | 250/368 |
| 2006/0038132 | A1 | * | 2/2006 | Hayashida | 250/370.11 |
| 2006/0067474 | A1 | * | 3/2006 | Schmitt | 378/102 |
| 2007/0110218 | A1 | * | 5/2007 | O'Dea et al. | 378/155 |
| 2008/0112535 | A1 | * | 5/2008 | Wojcik et al. | 378/62 |
| 2010/0202589 | A1 | * | 8/2010 | Ohta et al. | 378/98 |
| 2010/0246771 | A1 | * | 9/2010 | Hawver et al. | 378/98.2 |
| 2011/0049371 | A1 | | 3/2011 | Kobayashi | 250/361 R |
| 2011/0102184 | A1 | * | 5/2011 | Kito et al. | 340/600 |
| 2012/0039441 | A1 | | 2/2012 | Suwa et al. | 378/62 |

FOREIGN PATENT DOCUMENTS

JP        2001-154299        6/2001

* cited by examiner

*Primary Examiner* — Kiho Kim

(74) *Attorney, Agent, or Firm* — Fitzpatrick, Cella, Harper & Scinto

(57) ABSTRACT

A radiological image imaging apparatus includes: a radiation detection unit configured to detect radiation; a housing configured to contain the radiation detection unit; and a photo timer fixing member configured to fix a photo timer light receiving unit for measuring the radiation dose to the housing; wherein the photo timer fixing member is positioned such that the photo timer light receiving unit can be detached by separating cover members that form the surface of the housing.

9 Claims, 8 Drawing Sheets

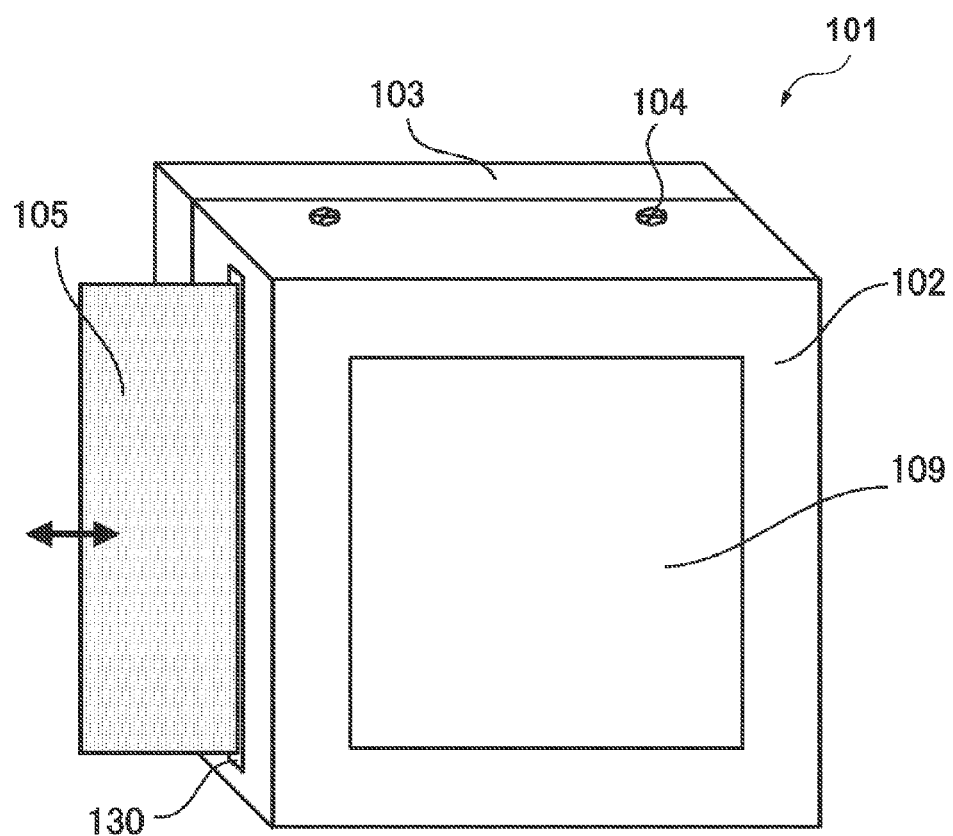

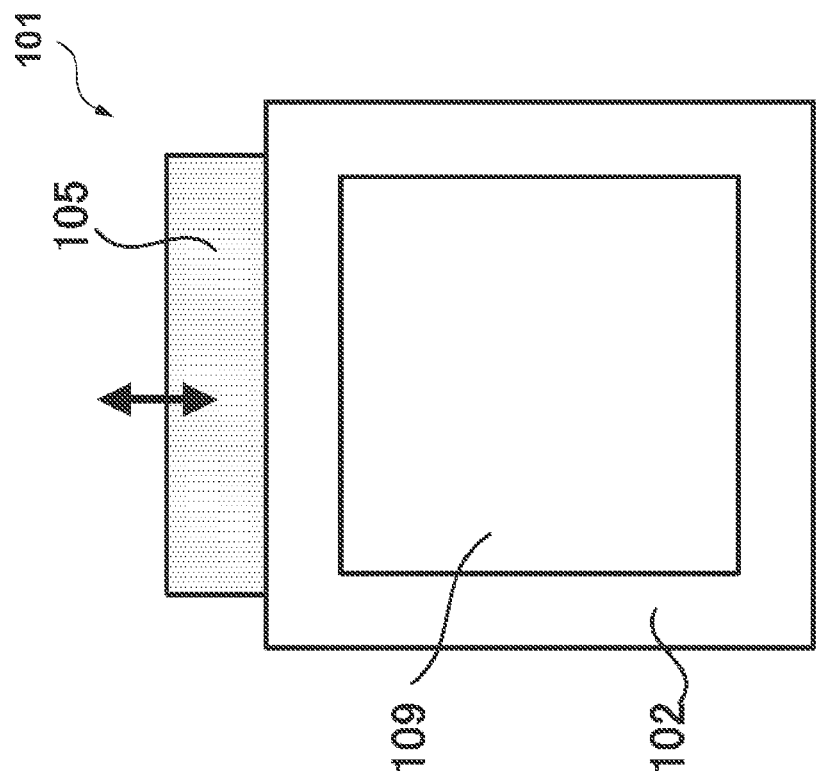
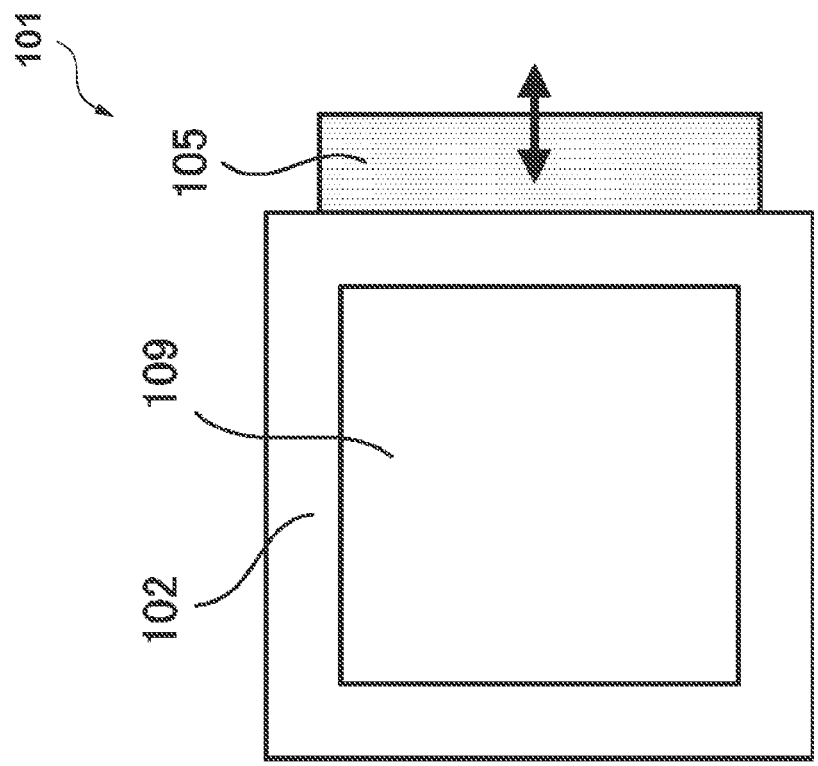

RADIATION IMAGING APPARATUS

BACKGROUND OF THE INVENTION

1. Field of the Invention

The present invention relates to a radiation imaging apparatus, and particularly relates to a radiation imaging apparatus that can incorporate an anti-scatter grid and a photo timer.

2. Description of the Related Art

Recently, digital radiation imaging apparatuses have been put into practice that directly digitalize a radiological image using radiation detector panels in which fluorescent substances are in close contact with large area solid-state image sensors, that is, so-called flat panel detectors (FPDs). Such digital radiation imaging apparatuses can immediately obtain a radiological image as digital information, and, thus, many advantages are provided such as reducing the amount of effort required for an imaging operation by an engineer or improving the efficiency in radiogram interpretation by a doctor.

Furthermore, in commonly performed radiography of the chest, the abdomen, or the like, imaging using an anti-scatter grid (hereinafter, referred to as a "grid") is performed in order to improve the contrast in a radiological image. There are a plurality of types of grids having different grid properties such as grid density, grid ratio, or focusing distance. In clinical practice, these grids are used in different manners in accordance with an object to be imaged. When a proper grid is selected and used, it is possible to obtain a high-contrast sharp image useful for diagnosis, and to prevent a patient from being overexposed to radiation and the irradiation time from being long. Meanwhile, in the case of objects to be imaged where the amount of scattered radiation generated is small, such as bones of extremities or infants, imaging is performed without using a grid.

An imaging apparatus has been developed in which a grid can be easily replaced by a plurality of grids having different properties and an imaging mode can be changed so as not to use a grid in response to a request to change imaging methods in this manner. Japanese Patent Laid-Open No. 2001-154299 (hereinafter, referred to as a "Document 1") discloses a configuration in which a grid is contained inside an imaging apparatus and can be attached and detached from the outside of the imaging apparatus. Furthermore, in the imaging apparatus of Document 1, the contained grid is conveyed by a drive mechanism configured from a motor and a cam. This configuration prevents grid stripes from being reflected on a radiological image. FIG. 7 is a vertical cross-sectional view of a schematic configuration of an ordinary radiation imaging apparatus having means for incorporating a grid into the imaging apparatus.

A radiation imaging apparatus 1 has a housing formed so as to contain internal components by combining two separate pieces; namely a cover member 2 functioning as a front cover that is brought into contact with a patient and a frame member 3 functioning as a rear cover. It is possible to access components inside the housing by detaching the cover member 2 from the frame member 3.

The imaging area on which radiation is incident on the cover member 2 is formed by a carbon plate 4 having a high X-ray transmission. Imaging is performed by pressing an area to be imaged (e.g., the chest) of a patient against the carbon plate 4. Accordingly, the cover member 2 and the carbon plate 4 are required to be strong enough to withstand the load applied by the patient. Ordinarily, the rigidity is secured by using a strong material for the cover member 2 or increasing the thickness. Furthermore, the strength of the carbon plate 4 is increased by fixing the carbon plate 4 using a reinforcing plate 5 or the like.

The radiation that has been transmitted through the carbon plate 4 passes through a grid member 6 that is disposed behind the carbon plate 4, and, thus, undesired scattered radiation diffusely reflected from the patient is removed. The grid member 6 is configured from a grid alone or a combination of a grid and a frame that surrounds and holds the grid. The grid member 6 is held by a grid containing member 7, and the grid containing member 7 is fixed to the frame member 3. The grid containing member 7 allows the grid member 6 to slide forward and backward (in directions perpendicular to the section of the diagram) for removal from the radiation imaging apparatus 1. A side face of the cover member 2 is provided with an opening through which the grid member 6 is to be inserted and removed, and the grid is attached to and detached from the radiation imaging apparatus 1 or replaced by a grid having another specification. Furthermore, in an imaging apparatus having a movable grid mechanism, a drive unit 10 for conveying the grid is attached to the frame member 3. The grid member 6 is conveyed along the guide of the grid containing member 7 by the actuating force from the drive unit 10.

Meanwhile, recently, means for performing imaging while keeping a grid still, obtaining radiological information containing grid stripes, and removing the grid stripes by the subsequent image processing has been also put into practice as new image processing algorithms are developed and processing speed is increased. An imaging apparatus using this sort of stationary grid is provided with positioning means for fixing the grid member 6 to a predetermined position on the grid containing member 7. The radiation that has been transmitted through the grid member 6 is incident on a radiation detection unit 8 constituting a radiation detector panel, and converted into digital information. The obtained signals are transmitted to image processing means, where an image used for diagnosis is generated.

Furthermore, in an ordinary radiation imaging apparatus, a photo timer has been conventionally used in order to obtain an image with an appropriate density by preventing underexposure or overexposure. A photo timer is an apparatus for blackening an obtained image to a constant degree and measures the dose of X-rays transmitted through an object in order to adjust the imaging time. A photo timer is also referred to as an auto exposure control (AEC). It is possible to simplify preset of imaging conditions by attaching the photo timer. A photo timer light receiving unit is a thin rectangular plate (film) having a thickness of 3 mm or less, and its receptor field is provided with a photo multiplier. The light receiving unit is disposed ordinarily behind the grid and in front of the sensor when viewed from the X-ray tube. If the dose of X-rays detected by the photo timer or the light receiving unit exceeds a set value, a signal is generated in order to stop radiation irradiation. Here, the shape or the position of the light receiving face (receptor field) varies depending on manufacturers. In recent digital imaging, the density can be corrected after imaging, and, thus, the demand for a photo timer for adjusting the exposure is lowered. However, since there is a strong demand for reducing exposure of a patient to radiation, use of a photo timer for preventing overexposure to radiation is becoming more important.

In order to properly control radiation irradiation using a photo timer, the correlation between the radiation dose obtained by the photo timer light receiving unit and the radiation dose obtained by the radiation detection unit 8 has to be high. Accordingly, the photo timer light receiving unit has to be disposed behind a grid where attenuation of incident radiation is high. In FIG. 7, the photo timer is disposed at a space 9 between the grid member 6 and the radiation detection unit 8.

Here, as a photo timer incorporated in a radiation imaging apparatus, photo timers having different specifications or shapes are requisite according to different manufacturers of X-ray generating apparatuses controlling radiation irradiation or according to different apparatus models even in the case of the same manufacturer. Accordingly, the operation that attaches a photo timer and adjusts connection with an X-ray generating apparatus cannot be performed at the time of shipment of a radiation imaging apparatus, and the operation that attaches the photo timer to the inside of the apparatus is performed by an engineer on site. As described above, the photo timer is attached to the inside of the radiation imaging apparatus so as to be positioned behind the grid, and, thus, in order to attach the photo timer, grid mechanism components have to be detached first. This process requires extra effort for an installation operation and a maintenance operation after the installation. Furthermore, there is another problem in that the durability and the strength of the apparatus tend to be lowered as the components are more frequently attached and detached as a result of the attachment of the photo timer.

Furthermore, medical apparatuses have to be prevented from going out of order through proper maintenance in order not to cause trouble to hospitals and patients, and have to be immediately restored when they are out of order. In the radiation imaging apparatus 1, the accessibility to the radiation detection unit 8, which is a main unit for obtaining an image, and the replaceability of the components are important. Conventionally, the radiation detection unit 8 is positioned behind the grid mechanism components and the photo timer components, and a large number of operation steps are necessary for accessing the radiation detection unit, which is an obstacle to a reduction in downtime.

SUMMARY OF THE INVENTION

The present invention was made in view of the above-described problems, and an embodiment thereof provides a radiation imaging apparatus in which the efficiency of the operation that attaches a photo timer and replaces internal components is improved.

According to one aspect of the present invention, there is provided a radiation imaging apparatus, comprising: a radiation detection unit configured to detect radiation; a housing configured to have a rear cover that holds the radiation detection unit and a front cover that has a radiation incident surface and is combined with the rear cover, and to internally contain the radiation detection unit; a grid holding unit configured to be fixed to an inner wall of the front cover, and to hold a grid member inside the housing; and a holding unit configured to be fixed to an inner wall of either the rear cover or the front cover, and to hold a photo timer light receiving unit between the grid holding unit and the radiation incident surface of the radiation detection unit.

Further features of the present invention will become apparent from the following description of exemplary embodiments with reference to the attached drawings.

BRIEF DESCRIPTION OF THE DRAWINGS

FIGS. 5A to 5C are explanatory views of radiation imaging apparatuses according to an embodiment.

DESCRIPTION OF THE EMBODIMENTS

Hereinafter, some preferred embodiments of the present invention will be described with reference to the attached drawings.

Figure 1:
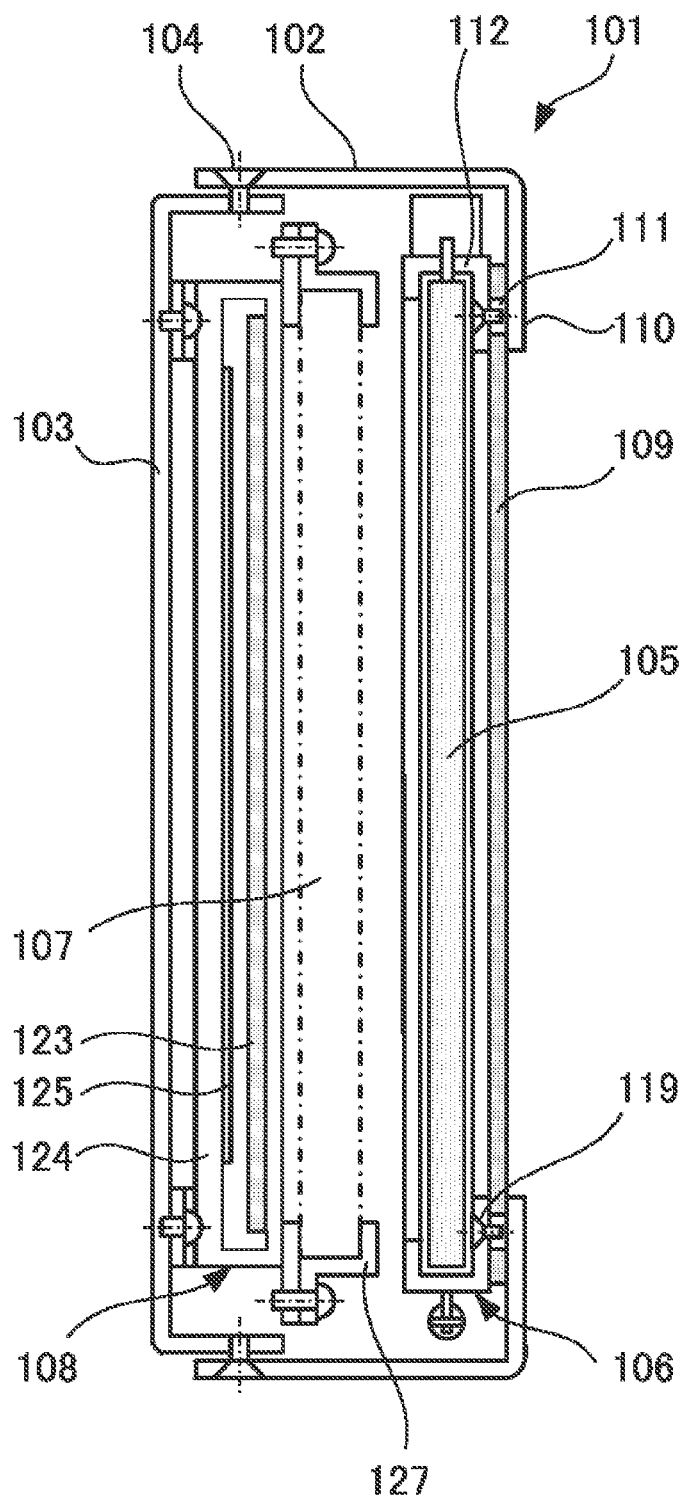
FIG. 1 is a vertical cross-sectional view of a radiation imaging apparatus according to an embodiment.

FIGS. 1 to 4 are views illustrating a first embodiment. FIG. 1 is a vertical cross-sectional showing the structure of a radiation imaging apparatus. In FIG. 1, 101 denotes a radiation imaging apparatus, and the radiation incident side is shown on the right in the diagram. The radiation imaging apparatus 101 includes a housing configured from a cover member 102 functioning as a front cover and a frame member 103 functioning as a rear cover. The frame member 103 has an attachment unit that is fixed to a stand when used for imaging with the patient standing and that is fixed to a table when used for imaging with the patient lying down. Both the cover member 102 and the frame member 103 are members that form the surface of the housing. The cover member 102 and the frame member 103 are connected to each other by fixing members 104. A grid containing unit 106 functioning as a grid holding unit that contains a grid member 105 in a detachable manner, a photo timer light receiving unit 107 that measures an irradiated radiation dose, and a radiation detection unit 108 that digitalizes a radiological image are arranged inside the housing.

The cover member 102 is configured from a carbon plate 109 having an excellent X-ray transmission and a cover frame member 110 in which the X-ray incident area is open in the shape of a quadrangle. Boss members 111 each having a hole at the center are arranged at a plurality of positions on each of four sides around the opening of the cover frame member 110. The carbon plate 109 has holes formed at positions corresponding to the boss members 111, and is attached such that its peripheral portion is in close contact with the inner wall of the cover frame member 110. Meanwhile, a side face of the cover frame member 110 is provided with a slot-shaped opening (an opening 130 shown in FIG. 5A, for example) through which the grid member 105 is inserted.

Figure 2:
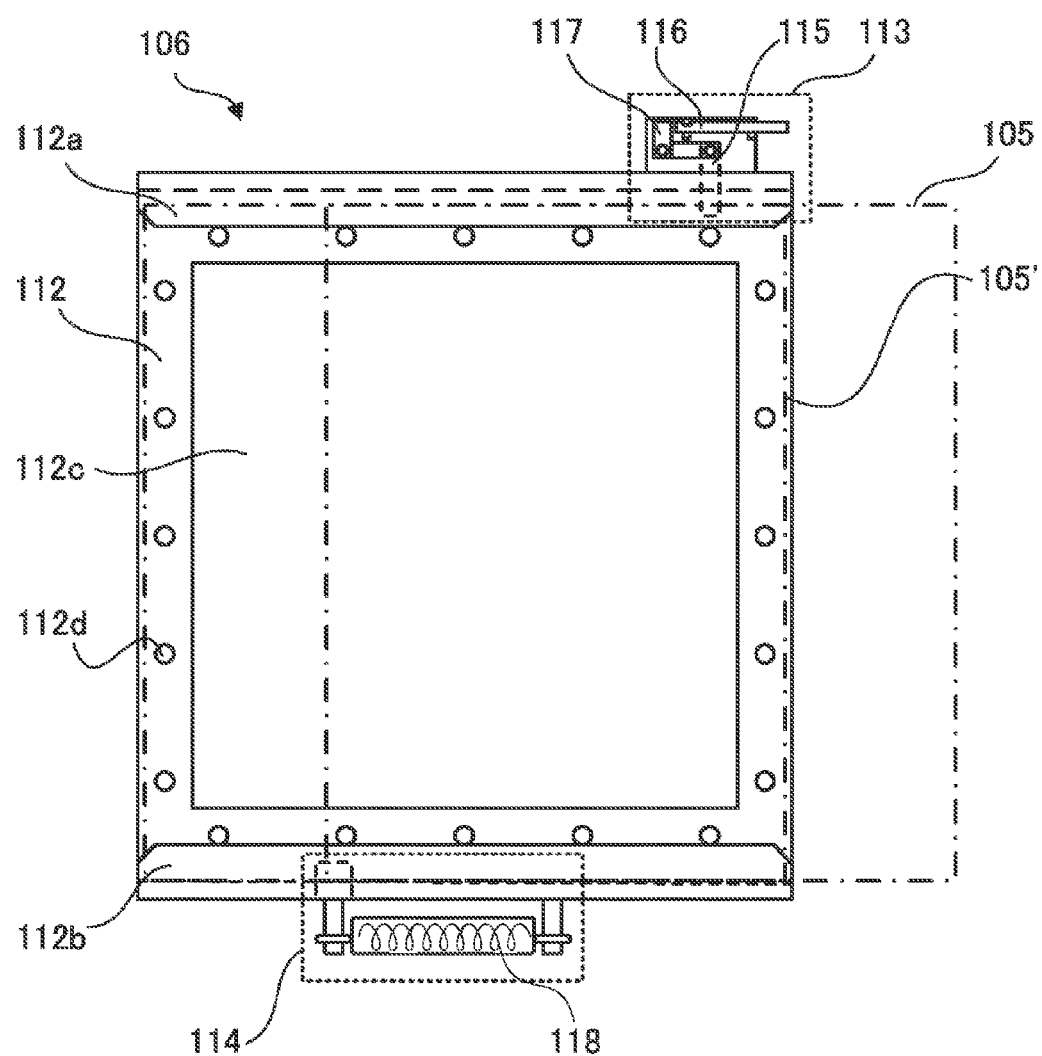
FIG. 2 is an explanatory view of a grid containing unit according to the embodiment.

FIG. 2 is a rear view (side opposite the radiation incident side) of the grid containing unit 106 contained in the housing. The grid containing unit 106 is configured from a grid guide member 112 that holds the grid member 105, a lock mechanism 113 that performs positioning of the grid, and an eject mechanism 114.

The grid guide member 112 is provided with U-shaped rail units 112a and 112b at upper and lower positions opposing each other, and holds the inserted grid member 105 such that it can slide leftward and rightward in the diagram. The center corresponding to the imaging area of the grid guide member 112 is provided with a quadrangular opening 112c, through which incident radiation passes.

The lock mechanism 113 has a function of regulating and locking leftward and rightward movement of the grid member 105 when it has been inserted to a predetermined position indicated by 105'. The lock mechanism 113 can have a configuration, for example, in which a lock shaft 115 is fitted to a recess formed in the grid member 105 using a link mechanism. The lock can be released, for example, using a mechanism in which, when a shaft 116 is pressed from the outside, a link member 117 rotates to move the lock shaft 115 upward.

The eject mechanism 114 has a function of ejecting the inserted grid member 105. When the grid member 105 is inserted, an elastic force is stored in a spring 118, and biases the grid member 105 rightward in the drawing. When the lock shaft 115 of the lock mechanism 113 is released, the grid member 105 is ejected due to this biasing force. This configuration improves the ease of the operation that takes out the grid.

Holes 112*d* that match the positions of the boss members 111 of the cover frame member 110 are arranged around the opening 112*c* of the grid guide member 112. Fixing members 119 (FIG. 1) use the holes 112*d* to combine the grid guide member 112 and the cover frame member 110 such that the carbon plate 109 is sandwiched therebetween.

The above-described structure improves the rigidity of a portion around the opening of the cover frame member 110 to which the load is applied by a patient, due to the structure of the grid guide member 112. Since the grid guide member 112 uses the rail units 112*a* and 112*b* with a shape having an excellent flexural rigidity, the flexural rigidity can be significantly improved. Furthermore, since the strength of the cover frame member 110 is improved in this manner, the amount of the carbon plate 109 warped as a result of the load is reduced, which, together with a reduction in the number of constituent components, can reduce the distance from the carbon plate 109 to the grid member 105. This arrangement can reduce the distance from the surface of the carbon plate 109 to the detection face of the radiation detection unit 108, and suppress the scale of enlargement of a radiological image, which causes geometric blurring (an unfocused image).

Furthermore, in the description above, an example has been described in which the cover member 102 has two separate constituent components; namely the carbon plate 109 and the cover frame member 110, but they can be integrally formed using a resin material having a good radiation transmission. Also in this case, the configuration in which the grid guide member 112 is fixed to the cover member 102 can improve the rigidity of the resin cover that usually has a rigidity lower than that of a metal cover.

The grid containing unit 106 functioning as a grid holding unit for holding the grid member 105 is fixed to the inner wall of the cover member 102 functioning as a cover on the X-ray tube side, that is, a front cover. On the other hand, the radiation detection unit 108 is fixed to the inner wall of the frame member 103 functioning as a rear cover. The radiation detection unit 108 has a radiation detector panel 123 that has a detection face for detecting radiation, an electric board 125 that is for converting the radiation dose on the detection face into electrical signals, and a support member 124 that supports the radiation detector panel 123 and the electric board 125. Image signals obtained by the radiation detection unit 108 are transmitted to an image processing apparatus and images for diagnosis are generated.

Figure 3:
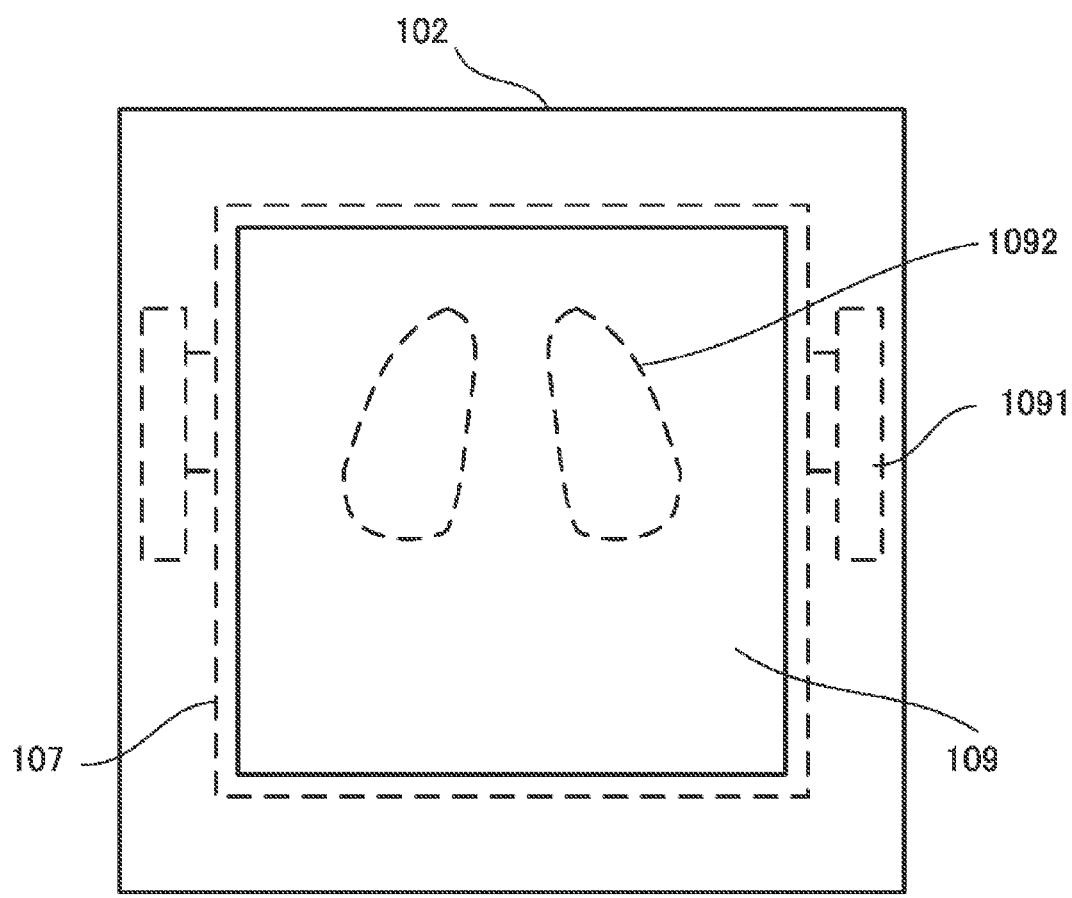
FIG. 3 is a view illustrating the arrangement of a photo timer.

A photo timer fixing member 127 is disposed between the detection face of the radiation detection unit 108 and the grid member 105. The photo timer fixing member 127 has an adjustment mechanism such that various photo timer light receiving units having different shapes or thicknesses can be fixed. FIG. 3 is a view illustrating the arrangement of the photo timer light receiving unit 107 in the radiation imaging apparatus 101 according to this embodiment. The photo timer light receiving unit 107 is fixed by the photo timer fixing member 127 to the position as shown in FIG. 3. That is to say, the photo timer light receiving unit 107 is fixed to the inner wall of the frame member 103 functioning as a rear cover. In the example in FIG. 1, the photo timer light receiving unit 107 is fixed via the radiation detection unit 108 to the inner wall of the frame member 103.

The photo timer light receiving unit 107 receives radiation in order to measure the dose of radiation incident on the cover member 102. The photo timer light receiving unit 107 is disposed so as to oppose a radiation incident surface formed by the carbon plate 109. Receptor fields 1092, which are areas where the radiation dose is to be detected, can be set in the photo timer light receiving unit 107. The dose of radiation (the amount of light) irradiated on the receptor fields 1092 is converted by a photoelectric conversion unit 1091 into electrical signals and stored. When the accumulated dose of radiation irradiated on the receptor fields 1092 exceeds a predetermined value, the photoelectric conversion unit 1091 outputs a signal indicating to that effect. The signal output from the photoelectric conversion unit 1091 is used to perform control for stopping radiation irradiation and to detect imaging completion.

In the thus configured radiation imaging apparatus 101 according to this embodiment, when a user tries to access the inside of the apparatus, the connection by the fixing members 104 is released and the cover member 102 is separated from the frame member 103. The grid containing unit 106 and the inserted grid member 105 are removed in one piece with the cover member 102 at the same time as the operation that separates the cover member 102. Then, an attachment space of the photo timer light receiving unit 107 is exposed at the top of the opening of the remaining frame member 103. This configuration allows the photo timer light receiving unit 107 to be easily attached. Furthermore, the configuration allows the radiation detection unit 108 to be easily accessed.

Figure 4:
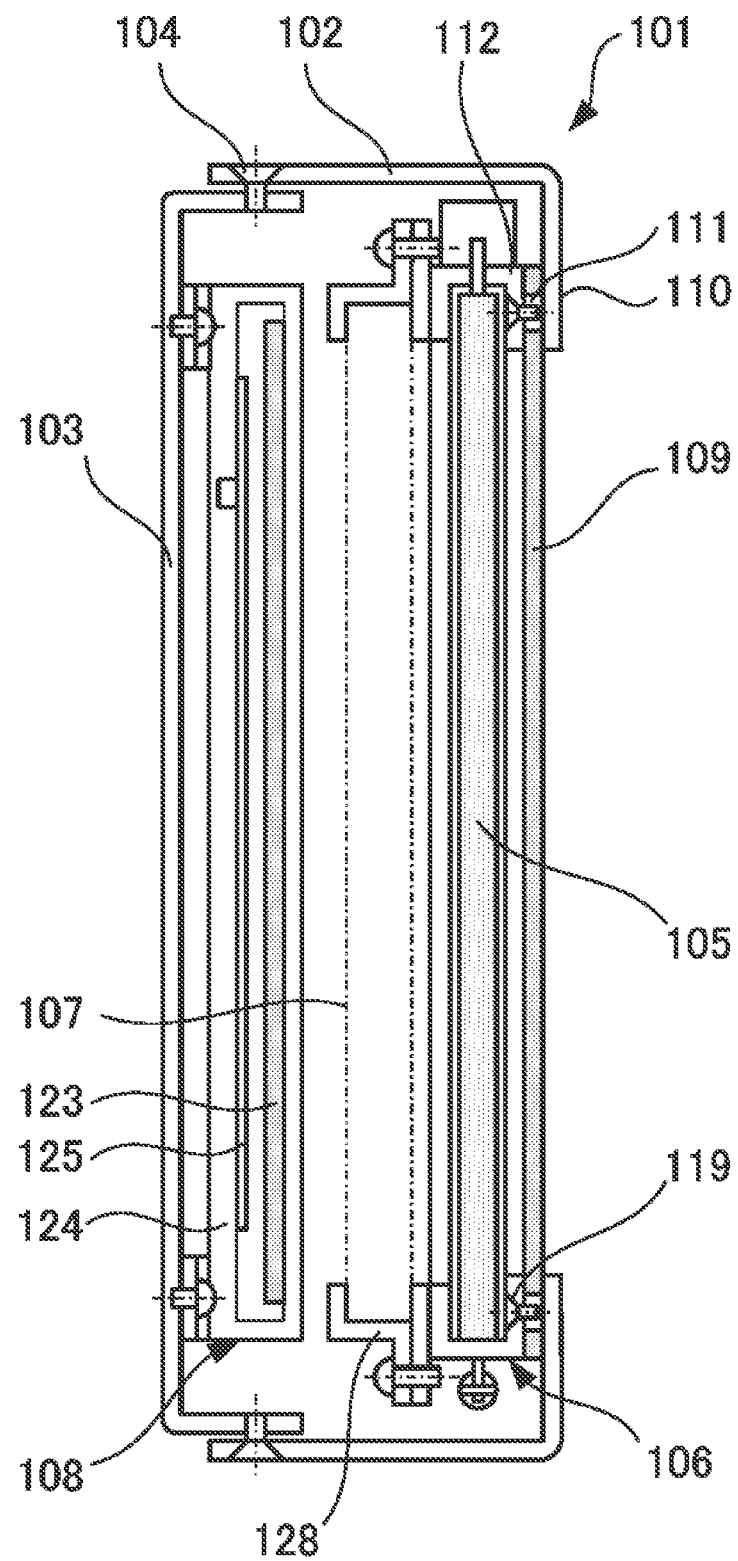
FIG. 4 is a vertical cross-sectional view of a radiation imaging apparatus according to a modified example of the embodiment.

FIG. 4 is a modified example of the foregoing embodiment. Although the photo timer fixing member 127 is disposed close to the frame member 103 in FIG. 1, a photo timer fixing member 128 is disposed behind the grid containing unit 106 in FIG. 4. That is to say, the photo timer light receiving unit 107 is fixed to the inner wall of the cover member 102 functioning as a front cover. In the example in FIG. 4, the photo timer light receiving unit 107 is fixed via the grid containing unit 106 to the inner wall of the cover member 102. In this configuration, if the cover member 102 is separated from the frame member 103, the photo timer light receiving unit 107 attached to the cover member 102 side is exposed. Meanwhile, the radiation detection unit 108 is exposed at the top on the frame member 103 side. This configuration allows the accessibility to the radiation detection unit to be further improved while maintaining the ease of the operation that attaches the photo timer.

As described above, according to the first embodiment, since the configuration has been applied in which the grid containing unit 106 can be separated in one piece with the cover member 102 from the frame member, the operation that attaches or replaces photo timers can be easily performed, and an improvement can be expected in the efficiency of installation or maintenance operations. Furthermore, according to the configuration in FIG. 4, it becomes easy to access the radiation detection unit 108, which is a main unit of the radiation imaging apparatus 101, thereby further reducing the downtime when restoring an apparatus that has gone out of order. Furthermore, since the number of times of the fixing members 104 being attached and detached according to the operations that attach or replace the photo timer light receiving units 107 is reduced, the durability of the apparatus is improved and the strength can be maintained. Furthermore, since the grid guide member 112 of the grid containing unit 106 that contains the grid member 105 reinforces the cover member 102, the rigidity of the housing can be improved without increasing the number of components. Furthermore, while the rigidity of the housing is improved, the structure can be simplified and the cost can be lowered.

Here, although the photo timer light receiving unit 107 is disposed at a position that covers the radiation incident surface of the radiation detection unit 108 in the foregoing example, the photo timer light receiving unit may be disposed in a space between the radiation detection unit 108 and a side face of the housing. The point is that the photo timer light receiving unit 107 need only be able to measure the dose of radiation incident on the radiation detection unit 108 at a position close to the radiation detection unit 108. Furthermore, the fixing member need only be positioned such that the photo timer light receiving unit can be detached by moving the cover member apart from the frame member.

FIGS. 5A to 5C are explanatory views of a second embodiment. This embodiment is the same as the first embodiment in that the grid containing unit can be separated in one piece with the cover member from the main body of the radiation imaging apparatus 101. However, the second embodiment is different from the first embodiment in that means for changing the pulling direction of the grid member 105 when attaching the separated cover member 102 to the frame member 103 is provided.

When the grid member 105 is inserted from the outside so as to be contained in the radiation imaging apparatus 101, an operation in which the grid is inserted or pulled out via a side face is safe and easy. Here, in this case, a side face of the radiation imaging apparatus 101 has to be provided with a space via which the grid is to be pulled out, the space having a length substantially the same as the horizontal size of the grid. However, depending on the conditions of an examination room that is used as an installation location, there are cases in which it is difficult to secure this space. Furthermore, in other cases, there are restrictions in the installation location in order to secure this space. Thus, in the second embodiment, the pulling direction of the grid member 105 can be changed, thereby improving the degree of freedom in installing the radiation imaging apparatus.

In FIG. 5A, the housing of the radiation imaging apparatus 101 is configured from the cover member 102 and the frame member 103 which are connected to each other by the fixing members 104. The grid member 105 can be attached and detached via the opening 130 in the left side face with respect to the radiation incident direction. In this state, the cover member 102 is separated from the frame member 103 by releasing the connection by the fixing members 104. With the internal configuration similar to that of the first embodiment, the grid containing unit and the grid member 105 are separated in one piece with the cover member 102 from the frame member 103.

If the pulling direction of the grid member 105 is set to be on the right side as shown in FIG. 5B, the cover member 102 is caused to be combined with the frame member 103 by rotating the separated cover member 102 by 180 degrees with respect to the state in FIG. 5A. Alternatively, in the case of an installation location where it is difficult to secure a space both in leftward and rightward directions such as a health-screening bus, as shown in FIG. 5C, the cover member 102 is rotated and combined with the frame member 103 such that the grid member 105 is pulled out upward or downward. Here, the cover member 102 and the frame member 103 are configured such that they can be combined with each other in all states shown in FIGS. 5A to 5C. Furthermore, a hole for fixing the cover member 102 and the frame member 103 is positioned so as to be a match even in the above-described rotated state, and the cover member 102 and the frame member 103 are fixed to each other by the fixing members 104 in each state. Here, in the case where the grid member is pulled out in the vertical direction as shown in FIG. 5C, the grid array direction inside the grid is rotated by 90 degrees with respect to the case where the grid member is pulled out in the horizontal direction. However, such a situation can be addressed by using a configuration of the grid member 105 in which the grid can be rotated by 90 degrees and attached to a frame for holding the grid.

As another embodiment, the photo timer light receiving units can be replaced via a side face of the housing. Although the basic configuration is the same as those of the foregoing embodiments, in this embodiment, a detachable member that forms the surface of the housing is provided on the side face of the housing, the member being different from the cover member 102 and the frame member 103. The fixing member 127 of the photo timer light receiving unit 107 is exposed via an opening of the housing formed by removing this member from the side face of the housing. Furthermore, the photo timer light receiving unit 107 can be removed from the housing by releasing the connection between the photo timer light receiving unit 107 and the photo timer fixing member 127 via this opening.

When the positional arrangement is made such that the photo timer light receiving unit can be detached by separating the member that forms the side face of the housing in this manner, the efficiency of the operations with respect to the attachment and the detachment of the photo timer light receiving unit 107 can be improved. Furthermore, the durability and the strength can be maintained compared with the case in which the cover member 102 of the housing is attached and detached.

As described above, according to the foregoing embodiments, since the grid containing member is removed in one piece with the cover member, the operation that attaches or replaces photo timers can be easily performed, and the efficiency of installation or maintenance operations is improved. Furthermore, it becomes easy to access the radiation detection unit, which is a main unit of the radiation imaging apparatus, thereby reducing the downtime when restoring an apparatus that has gone out of order. Moreover, the rigidity of the housing can be improved without increasing the number of constituent components. Furthermore, since the direction of the opening for inserting or pulling out the grid member can be changed to a plurality of directions with respect to the frame member, it is possible to make installation easy and to improve the degree of freedom in installation.

According to the present invention, the efficiency of the operation that attaches a photo timer and replaces internal components can be improved.

Figure 6:
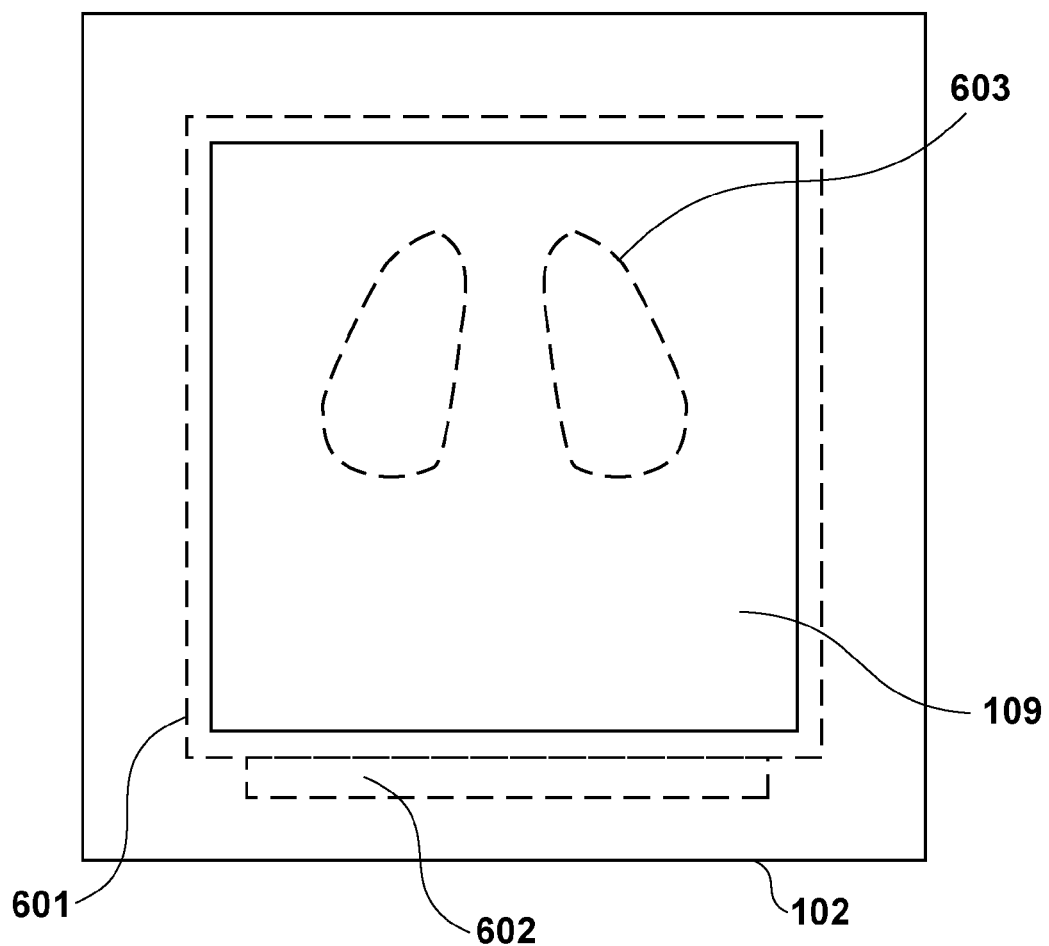
FIG. 6 is a view illustrating a photo timer light receiving unit using an ionization chamber.
Figure 7:
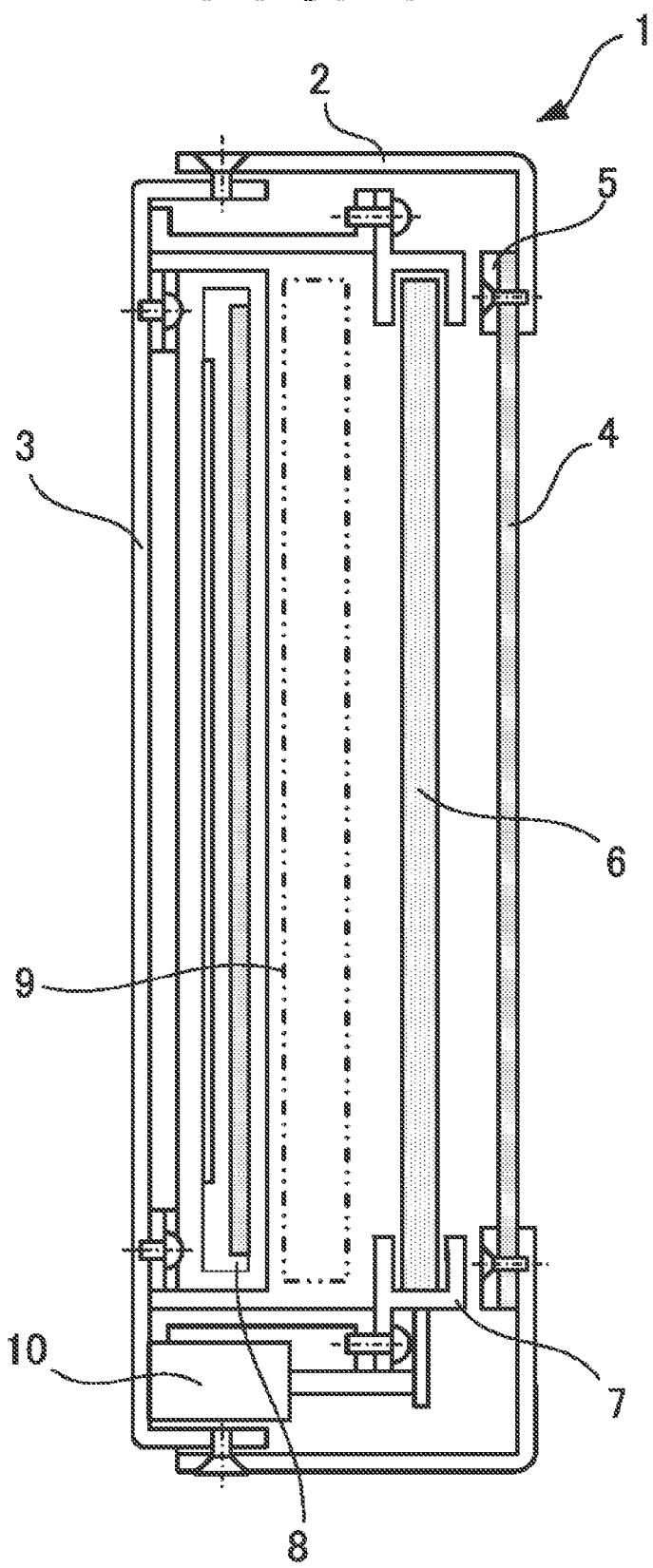
FIG. 7 is a configuration view of an ordinary radiation imaging apparatus.

In aforementioned embodiment a photomultiplier is used as a photo timer light receiving unit 107. In an alternative embodiment, an ionization chamber may be used. FIG. 6 is a view illustrating a photo timer light receiving unit using an ionization chamber 601. The photo timer light receiving unit includes an ionization chamber 601, and an amplifier unit 602. A detection area 603 can be set on the radiation incident surface of the photo timer light receiving unit. When the photo timer light receiving unit receives radiation, gas enclosed in the ionization chamber 601 ionizes, which causes a difference of current values between electrodes in the ionization chamber 601. The photo timer light receiving unit detects dose of radiation by amplifying and measuring the difference of current values.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-042655, filed Feb. 28, 2011, which is hereby incorporated by reference herein in its entirety.

What is claimed is:

1. A radiation imaging apparatus, comprising:
   a radiation detection unit configured to detect radiation;
   a housing configured to have a rear cover that holds the radiation detection unit and a front cover that has a radiation incident surface and is combined with the rear cover, and to internally contain the radiation detection unit;
   a grid holding unit configured to be fixed to an inner wall of the front cover, and to hold a grid member inside the housing; and
   a holding unit configured to be fixed to an inner wall of either the rear cover or the front cover, and to hold a photo timer light receiving unit between the grid holding unit and a radiation incident surface of a radiation detection unit.

2. The apparatus according to claim 1, wherein the holding unit is fixed to the rear cover.

3. The apparatus according to claim 1, further comprising fixing means for connecting the rear cover and the front cover so as to form the housing.

4. The apparatus according to claim 3,
   wherein the front cover is provided with an opening through which the grid member is to be inserted from the outside into the grid holding unit, and
   the fixing means can connect the rear cover and the front cover in a plurality of types of states where the opening is oriented in different directions when the housing is formed.

5. The apparatus according to claim 1, wherein the radiation incident surface of the front cover is formed by a carbon plate.

6. The apparatus according to claim 1,
   wherein the housing is provided with an opening through which the grid member is to be inserted from the outside into the grid holding unit, and
   the grid holding unit has a guide member along which the grid member inserted via the opening slides to be guided inward, and the guide member is attached to the front cover, thereby improving the strength of the front cover.

7. The apparatus according to claim 6,
   wherein the front cover has a carbon plate that forms the radiation incident surface and a cover frame member to which a peripheral portion of the carbon plate is fixed and attached, and
   the carbon plate is sandwiched and fixed between the guide member and the cover frame member.

8. The apparatus according to claim 1, wherein the photo timer light receiving unit is exposed so as to be capable of being detached, by separating the rear cover and the front cover that form the housing.

9. An apparatus for radiation imaging using a radiation detection unit, comprising:
   a housing configured to have a rear cover that holds the radiation detection unit and a front cover that has a radiation incident surface and is combined with the rear cover, and to internally contain the radiation detection unit;
   a grid holding unit configured to be fixed to an inner wall of the front cover, and to hold a grid member inside the housing; and
   a holding unit configured to be fixed to an inner wall of one of the rear cover and the front cover, and to hold a photo-timer light receiving unit between the grid holding unit and a radiation incident surface of the radiation detection unit.

* * * * *